United States Patent
Reed et al.

(12)

(10) Patent No.: US 6,379,951 B1
(45) Date of Patent: Apr. 30, 2002

(54) COMPOUNDS FOR IMMUNOTHERAPY OF BREAST CANCER AND METHODS FOR THEIR USE

(75) Inventors: Steven G. Reed; Jiangchun Xu, both of Bellevue, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/118,627

(22) Filed: Jul. 17, 1998

Related U.S. Application Data

(63) Continuation-in-part of application No. 08/998,253, filed on Dec. 24, 1997, now abandoned.

(51) Int. Cl.[7] .................. C07H 21/04; C07H 21/02; C12N 1/20; C12N 15/00; C12N 5/00

(52) U.S. Cl. ............... 435/325; 536/23.5; 536/23.1; 435/252.33; 435/252.8; 435/254.2; 435/320.1; 435/352; 435/358; 435/363; 435/365; 435/366

(58) Field of Search ....................... 536/23.1, 23.5; 435/320.1, 252.33, 252.8, 254.2, 325, 352, 358, 363, 365, 366

(56) References Cited

U.S. PATENT DOCUMENTS 5,985,847 A * 11/1999 Carson et al.

FOREIGN PATENT DOCUMENTS

| EP | 0679716 A | 11/1995 |
|---|---|---|
| WO | 9818945 | * 5/1988 |
| WO | WO 94/21287 | 9/1994 |
| WO | WO 94/23728 | 10/1994 |
| WO | WO 95/11986 | 5/1995 |
| WO | WO 95/19783 | 7/1995 |
| WO | WO 97/02280 | 1/1997 |
| WO | WO 97/25426 | 7/1997 |
| WO | WO 97/34921 | 9/1997 |
| WO | WO 99/33869 | 7/1999 |

OTHER PUBLICATIONS

Alberts et al, Ed., Molecular Biology of the Cell (textbook), 3rd edition, p. 465, 1994.*
Shantz and Pegg, "Translational regulation of ornithine decarboxylase and other enzymes", International J of Biochemistry and Cell Biology, vol. 31, pp. 107–122, 1999.*
McClean and Hill, "Evidence of post–translational regulation of p–glycoprotein", European J. of Cancer, vol. 29A, pp. 2243–2248, 1993.*
Fu et al, "Translational regulation of human p53 gene expression", EMBO, vol. 15, pp. 4392–4401, 1996.*
Davis et al, "Plasmid DNA is superior to viral vectors for direct gene transfer into adult mouse skeltal muscle", Hum Gene Ther, vol. 4, pp. 733–740, Dec. 1993.*
Wickham, T.J., "Targeting Adenovirus", Gene Therapy, vol. 7, pp. 110–114, Jan. 2000.*

Crystal, R.G., "In vivo and ex vivo gene therapy strategies to treat tumors using adenovirus gene transfer vectors", Cancer Chemotherapy and Pharmacology, vol. 43, Suppl., pp. S90–S99, May 1999.*
Ada, G., "The coming age of immunotherapy", Immunology and Cell biology, vol. 77, pp. 180–185, 1999.*
Gura, T., "Systems for identifying new drugs are often faulty", Science, vol. 278, pp. 1041–1042, Nov. 1997.*
Matsui, et al, "A model for CD+8 CTL tumor immunosurveillance and regulation of tumor escape by CD+4 cells", J Immunology, vol. 163, pp. 184–193, 1999.*
Hiraki et al, "Loss of HLA haplotype in lung cancer cell lines:Implications for immunosurveillance of altered HLA Class I/II phenotypes in cancer", Clinical Cancer Research, Vo. 5, pp. 933–936, Apr. 1999.*
Welt and Ritter, "Antibodies in the therapy of colon cancer", Seminars in Oncology, vol. 26, pp. 683–690, Dec. 1999.*
Paul et al, "HLA–G expression in melanoma: a way fro tumor cells to escape from immunosurveilance", PNAS, vol. 95, pp. 4510–4515, Apr. 1998.*
Becker et al, "Tumor escape mechanisms from immunosurvillance", International Immunology, vol. 5, pp. 1501–1508, 1993.*
Blumenthal et al, "Physiological factors influencing radio-antibody uptake", International Journal of Cancer, vol. 51, pp. 935–941, 1992.*
Genebank Accession No: H 21977 (Jul. 6, 1995).*
Genebank Accession No: H 21976 (Jul. 6, 1995).*
Genebank Accession No: H 25624 (Jul. 10, 1995).*
Genebank Accession No: H 25577 (Jul. 10, 1995).*
Genebank Accession No: AA 34069 (Apr. 21, 1997).*
Genebank Accession No: R75793 (Jun. 6, 1995).*
Genebank Accession No: W72838 (Oct. 16, 1996).*
Genebank Accession No: W728737 (Oct. 16, 1996).*
Genebank Accession No: AA451680 (Jun. 5, 1997).*
Genebank Accession No: AA413174 (May 2, 1997).*
Genebank Accession No: AA124124 (Feb. 17, 1997).*
Genebank Accession No: AA299443 (Apr. 18, 1997).*
Genebank Accession No: D50995 (Sep. 14, 1995).*
Genebank Accession No: D59275 (Aug. 28, 1995).*
Genebank Accession No: D80022 (Feb. 9, 1996).*
Genebank Accession No: R78938 (Jun. 9, 1995).*
Genbank Accession No: N48289 (Feb. 14, 1996).*
Genbank Accession No: N49017 (Feb. 14, 1996).*
Genbank Accession No: AA163045 (Feb. 16, 1997).*

(List continued on next page.)

Primary Examiner—Anthony C. Caputa
Assistant Examiner—Karen A. Canella
(74) Attorney, Agent, or Firm—Seed Intellectual Property Law Group PLLC

(57) ABSTRACT

Compounds and methods for treating breast cancer are provided. The inventive compounds include polypeptides containing at least a portion of a breast tumor protein. Vaccines and pharmaceutical compositions for immunotherapy of breast cancer comprising such polypeptides, or DNA molecules encoding such polypeptides, are also provided, together with DNA molecules for preparing the inventive polypeptides.

10 Claims, No Drawings

OTHER PUBLICATIONS

Genbank Accession No: WO2878 (Apr. 18, 1996).*
Genbank Accession No: AA366357 (Apr. 21, 1997).*
Genbank Accession No: N59253 (Feb. 23, 1996).*
Genbank Accession No: N62351 (Mar. 1, 1996).*
Genbank Accession No: N76721 (Apr. 2, 1996).*
Genbank Accession # N54784 (Jan. 28, 1997).*
Genbank Accession # AA364013 (Apr. 21, 1997).*
Genbank Accession # AA857077 (Jun. 6, 1997).*
Genbank Accession # AA150963 (May 19, 1997).*
Genbank Accession # Z98046 (Jul. 13, 1998).*
Genbank Accession # AA 971201 (May 20, 1998).*
Genbank Accession # AA 703778 (Dec. 24, 1997).*
Genbank Accession # AA 535981 (Aug. 21, 1997).*
Genebank Accession # AA646568 (Oct. 28, 1997).*
Genebank Accession # AJ005890 (May 15, 1998).*
Genebank Accession # AA425487 (Oct. 16, 1997).*
Genebank Accession # AA746345 (Jan. 27, 1998).*
Genebank Accession # AA256631 (Aug. 6, 1997).*
Genebank Accession # AA243535 (Aug. 15, 1997).*
Genebank Accession # AA259166 (Aug. 15, 1997).*
Genebank Accession # AA962009 (May 15, 1998).*
Genebank Accession No: AA456968 (Jun. 6, 1997).*
Genebank Accession No: AA626243 (Oct. 15, 1997).*
Genebank Accession No: AA775552 (Feb. 5, 1998).*
Genebank Accession No: AA214632 (Aug. 13, 1997).*
Genebank Accession No: AA258236 (Aug. 13, 1997).*
Genebank Accession No: AA701126 (Dec. 19, 1997).*
Genebank Accession No: AA535894 (Aug. 21, 1997).*
Genebank Accession No: AA722353 (Jan. 2, 1998).*
Genebank Accession No: AA133706 (Jul. 31, 1997).*
Genebank Accession No: AA848022 (Mar. 31, 1998).*
Genebank Accession No: AA857 943 (Apr. 29, 1998).*
Genebank Accession No: AA856775 (Jun. 9, 1998).*

Bio: Critical Synergy: The Biotech Industry and Intl. Property Oct. 17, 1994 pp. 101, 103–104.*
Genbank Sequence Database, Accession No. AA478500, Aug. 8, 1997.
Genbank Sequence Database, Accession No. AA490863, Aug. 15, 1997.
Genbank Sequence Database, Accession No. AA552419, Sep. 5, 1997.
Genbank Sequence Database, Accession No. AA610465, Oct. 30, 1997.
Genbank Sequence Database, Accession No. AA613497, Oct. 30, 1997.
Genbank Sequence Database, Accession No. T21968, Aug. 5, 1996.
Liang et al., "Differential Display and Cloning of Messenger RNAS from Human Breast Cancer Versus Mammary Epithelial Cells," *Cancer Research* 52:6966–6968, 1992.
Porter Jordan and Lippman, "Overview of the Biological Markers of Breast Cancer," *Breast Cancer* 8(1):73–100, 1994.
Schlom et al., "Strategies for the Development of Recominant Vaccines for the Immunotherapy of Breast Cancer," *Breast Cancer Research and Treatment* 38:27–39, 1996.
Watson and Fleming, "Isolation of Differentially Expressed Sequence Tags from Human Breast Cancer," *Cancer Research* 54:4598–4602, 1994.
Yee et al., "Isolation of Tyrosinase–Specific $CD8^+$ and $CD4^+$ T Cell Clones from the Peripheral Blood of Melanoma Patients Following In Vitro Stimulation with Recombinant Vaccinia Virus," *J. of Immunology* 157:4079–4086, 1996.
GenBank Accession No. AA749298, "*Homo sapiens* cDNA clone Image:1271152 3', mRNA sequence," Jan. 20, 1998.

* cited by examiner

SEQUENCE LISTING

```
<160> NUMBER OF SEQ ID NOS: 67

<210> SEQ ID NO 1
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 1 ttttttttttt tttttaggag aactgaatca aacagatttt attcaacttt t tagatgagg      60 aaaacaaatn atacgaaatn ngtcataaga aatgctttct tataccacta t ctcaaacca    120 ctttcaatat tttacaaaat gctcacgcag caaatatgaa aagctncaac a cttcccttt    180 gttaacttgc tgcaatnaat gcaactttaa canacataca aatttcttct g tatcttaaa    240 agttnaatta ctaattttaa tgatnttnct caagatnttt attcatatac t tttaatgac    300 tcnttgccna tacatacnta ttttctttac tttttttta cnatnggcca a cagctttca    360 ngcagnccnc aaaaatctta ccggttaatt acacggggtt gt                         402

<210> SEQ ID NO 2
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 2 ttttttttttt tttttaaag gtacacattt cttttcatt ctgtttnatg c agcaaataa      60 ttcgttggca tcttctctgt gatgggcagc ttgctaaaat tanactcagg c cccttagct    120 ncatttccaa ctnagcccac gctttcaacc nngccnaaca aagaaaatca g ttngggtta    180 aattctttgc tgganacaaa gaactacatt cctttgtaaa tnatgctttg t ttgctctgt    240 gcaaacncag attgaaggga anaagganac ttntggggac ggaaacaact n gnagaagca    300 gganccgccc agggncattt cctcaccatg cttaatcttg cnctcacttg c ngggcacca    360 ttaaacttgg tgcaaaaggc gcaattggtg nanggaaccc cacaccttcc t taaaaagca    420 gggc                                                                   424
```

<210> SEQ ID NO 3
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 3

```
ttttttttt ttttcccaa tttaaaaaag cctttttcat acttcaatta c accanactt      60
aatnatttca tgagtaaatc ngacattatt atttnaaaat ttgcatattt a aaatttgna   120
tcanttactt ccagactgtt tgcanaatga agggaggatc actcaagngc t gatctcnca   180
ctntctgcag tctnctgtcc tgtgcccggn ctaatggatc gacactanat g gacagntcn   240
cagatcttcc gttcttntcc cttccccaat ttcncaccnc tcccttctt n cccggatcn    300
tttggggaca tgntaatttt gcntatccta aaccctgccc gccangggtc c cnanctcag   360
gggtggttaa tgttcgncng gcttnttgac cncctgcgcc ctttnantcc n aaccccaag   420
c                                                                    421
```

<210> SEQ ID NO 4
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 4

```
ttttttatt tttttttcta tttntnntat ttnntgnggt tcctgtgtgt a attagnang    60
tgtgtatgcg tangtacnta tgtntgcata tttaacctgt tnccttcca t tttaaaat    120
aaaatctcaa natngtantt ggttnatggg agtaaanaga gactatngat n aattttaac  180
atggacacng tgaaatgtag ccgctnatca ntttaaaact tcattttgaa g gcctttnc   240
cctccnaata aaaatnccng gccctactgg gttaagcaac attgcatntc t aaagaaacc  300
acatgcanac nagttaaacc tgtgnactgg tcangcaaac cnanntggaa n anaagggnn  360
ttcncccan ggacantcng aatttttta acaaattacn atnccccccc n ggggagcc    420
tgt                                                                  423
```

<210> SEQ ID NO 5
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 5

```
acgaccacct natttcgtat ctttcaactc ttttcgaccg gacctcttat t cggaagcgt    60
tccaggaaga caggtctcaa cttagggatc agatcacgtt atcaacgctc t gggatcgct  120
gcaacctggc acttcaagga agtgcaccga tnacgtctag accggccaac a cagatctag  180
aggtggccaa ctgatcactg taggagctga ctggcaanan tcaaccgggc c ccaaccnag  240
agtgaccaan acnaccattn aggatcaccc acaggcactc ctcgtcctag g gccaaccna  300
ccaaacggct ggccaatggg ggggtttaat atttggttna aaaattgatt t taaa       355
```

<210> SEQ ID NO 6
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 6

```
tttttttttt ttttggaca ggaagtaaaa tttattggtn antattaana g ggggcagc      60
acattggaag ccctcatgan tgcagggccc gccacttgtc cagagggcca c nattgggga   120
tgtacttaac cccacagccn tctgggatna gccgcttttc agccaccatn t cttcaaatt   180
catcagcatt aaacttggta aanccccact tctttaagat ntgnatcttc t ggcggccag   240
naaacttgaa cttggccctg cgcagggcct caatcacatg ctccttgttc t gcagcttgg   300
tgcgnaagga cntaatnact tggccnatgt gaaccctggc cacantgccc t gggctttc    360
caaaggcacc tcgcaagcct ntttggancc tgnccgcccc ngcacaggga c aacatcttg   420
ttt                                                                   423
```

<210> SEQ ID NO 7
<211> LENGTH: 410
<212> TYPE: DNA
<213> ORGANISM: Homo sapien
<220> FEATURE:
<221> NAME/KEY: misc_feature
<222> LOCATION: (1)...(410)
<223> OTHER INFORMATION: n = A,T,C or G

<400> SEQUENCE: 7

```
ttcgcactgg ctaaaacaaa ccgccttgca aagttngaaa aatttatcaa t ggaccaaat    60
aatgctcata tccnacaagt tggtgaccgt tnttatnata aaaaaatgta t natgctcct   120
nanttgttgt acaataatgt tccaatttng gacnttcggc atctaccctg g ttcacctgg   180
gtaaatatca ggcagctttt gatggggcta ggaaagctaa cagtactcga a catgggaaa   240
gaggtctgct tcgccngtgt anatgggaaa naattccgtc ttgctcngat t tgtggactt   300
catattgttg tacatgcaga tgaatnngaa gaacttgtca actactatca g gatcgtggc   360
tttttnnaaa agctnatcac catgttggaa gcggcactng gacttgagcg              410
```

<210> SEQ ID NO 8
<211> LENGTH: 274
<212> TYPE: DNA
<213> ORGANISM: Homo sapien
<220> FEATURE:
<221> NAME/KEY: misc_feature
<222> LOCATION: (1)...(274)
<223> OTHER INFORMATION: n = A,T,C or G

<400> SEQUENCE: 8

```
tttttttttt ttttaggtc atacatattt tttattataa canatatntg t atatacata    60
taatatatgt gtatatatcc acgtgtgtgt gtgtgtatca aaaacaacan a antttagtg  120
atctatatct ntngctcaca tatgcatggg agataccagt aaaaaataag t naatctcca  180
taatatgttt taaaactcan anaaatcnga gagactnaaa gaaaacgttn a tcannatga  240
ttgtngataa tcttgaanaa tnacnaaaac atat                                274
```

<210> SEQ ID NO 9

```
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 9
tttttttttt ttttgtgcct tattgcaccg gcnanaactt ctagcactat a ttaaactca      60 ataagagtga taagtgtgaa atccttgcc ttctctttaa tcttaatgna n aggcatctg     120 gttttttcacc attaantgta ataatggctn tatgtatttt tatnnatggt c ttnatggag   180 ttaaaaaagt tttcctctnt ccctngttat ctaanagttt tnatcaaaaa t gggtataat   240 atttngttca gtactttttnc ctgcacctat agatatgatn ctgttatttt t tcttcttng  300 cctnnanata tgatggatna ca                                             322

<210> SEQ ID NO 10
<211> LENGTH: 425
<212> TYPE: DNA
<213> ORGANISM: Homo sapien
<220> FEATURE:
<221> NAME/KEY: misc_feature
<222> LOCATION: (1)...(425)
<223> OTHER INFORMATION: n = A,T,C or G

<400> SEQUENCE: 10
tttttttttt tttttattct gcagccatta aatgctgaac actagatnct t atttgtgga    60 ggtcacaaaa taagtacaga atatnacaca cgccctgccc ataaaaagca c agctcccag  120 ttctatattt acaatatctc tggaattcca ccttcccttc taatttgact a atatttctg  180 cttctcaggc agcagcgcct tctggcaacc ataagaacca acntgnggac t aggtcggtg  240 ggccaaggat caggaaacag aanaatggaa gnagcccccn tgacnctatt a anctntnaa  300 actatctnaa ctgctagttt tcaggcttta aatcatgtaa natacgtgtc c ttnttgctg  360 caaccggaag catcctagat ggtacactct ctccaggtgc caggaaaaga t cccaaatng  420 caggn                                                               425

<210> SEQ ID NO 11
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 11
ttttnttant ttttttancc nctnntccnn tntgttgnag ggggtaccaa a tttctttat    60 ttaaaggaat ggtacaaatc aaaaaactta atttaatttt tnggtacaac t tatagaaaa  120 ggttaaggaa accccaacat gcatgcactg ccttggtaac cagggnattc c cccncggct  180 ntggggaaat tagcccaang ctnagctttc attatcactn tcccccaggg t ntgcttttc  240 aaaaaaattt nccgccnagc cnaatccggg cnctcccatc tggcgcaant t ggtcacttg  300 gtcccccnat tctttaangg cttncacctn ctcattcggg tnatgtgtct c aattaaatc  360 ccacngatgg gggtcatttt tntcnnttag ccagtttgtg nagttccgtt a ttganaaaa  420 ccan                                                                424
```

-continued

```
<210> SEQ ID NO 12
<211> LENGTH: 426
<212> TYPE: DNA
<213> ORGANISM: Homo sapien
<220> FEATURE:
<221> NAME/KEY: misc_feature
<222> LOCATION: (1)...(426)
<223> OTHER INFORMATION: n = A,T,C or G

<400> SEQUENCE: 12 ttttttttttt ttttncttaa aagcttttat ctcctgctta cattacccat c tgttcttgc      60 atgttgtctg cttttccac tagagccctt aacaacttaa tcatggttat t ttaagggct      120 ctaataattc cnaaactggt atcataaata agtctcgttc tnatgcttgt t ttctctcta     180 tcacactgtg ttngttgctt tttnacatgc tttgtaattt ttggctgaaa g ctgaaaaat    240 nacatacctg gttntacaac ctgaggtaan cagccttnta gtgtgaggtt t tatatntta    300 ctggctaaga gctnggcnct gttnantant tgttgtanct ntatatgcca n aggctttna   360 tttccnctng tgtccttgct tnagtacccc attntttag gggttcccta n aaactctat    420 ctnaat                                                                  426

<210> SEQ ID NO 13
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 13 ttttttttttt tttttnagat agactctcac tctttcgccc aggctggagt g cagtggcgc     60 aatcaaggct cactgcaacc tctgccttat aaagcatttn ctaaaggtac a agctaaatt   120 ttaaaatat ctctncacaa ctaatgtata acaaaaatta gttctacctc a taaacncnt   180 ggctcagccc tcgnaacaca tttccctgtt ctcaactgat gaacactcca n aaacagaac   240 anatntaagc ttttccaggc ccagaaaagc tcgcgagggg atttgctntg t gtgtgacac    300 acttgccacc ctgtggcagc acagctccac acntgctttg gccgcatttt g caagttctc   360 tgtaanccc ctgnaagacc cggatcagct gggtngaaat tgcangcnct c ttttggca    419

<210> SEQ ID NO 14
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 14
aanccattgc caagggtatc cggaggattg tggctgtcac aggtnccgag g cccanaagg     60 ccctcaggaa agcaaagagc ttgaaaaatg tctctctgtc atggaagccn a agtgaaggc   120 tcanactgct ccaacaagga tntgcanagg gagatcgcta accttggaga g gccctggcc   180 actgcagtcn tccccanntg gcagaaggat gaattgcggg agactctcan a tcccttang   240 gaaggtcgtg gatnacttgg accgagcctc nnaagccaat ntccagaaca a gtgttggag   300 aagacaaagc anttcatcga cgccaacccc naccggcctc tnttctcctg g anattgana   360 gcggcgcccc cgcccagggc cttaataanc cntgaagctn                             400
```

<210> SEQ ID NO 15
<211> LENGTH: 395
<212> TYPE: DNA
<213> ORGANISM: Homo sapien
<220> FEATURE:
<221> NAME/KEY: misc_feature
<222> LOCATION: (1)...(395)
<223> OTHER INFORMATION: n = A,T,C or G

<400> SEQUENCE: 15

| | | | | | |
|---|---|---|---|---|---|
| tgctttgctg | cgtccaggaa | gattagatng | aanaatacat | attgatttgc c | aaatgaaca 60 |
| agcgagatta | gacntactga | anatccatgc | aggtcccatt | acaaagcatg g | tgaaataga 120 |
| tgatgaagca | attgtgaagc | tatcggatgg | ctttnatgga | gcagatctga g | aaatgtttg 180 |
| tactgaagca | ggtatgttcg | caattcgtgc | tgatcatgat | tttgtagtac a | ggaagactt 240 |
| catgaaagcn | gtcagaaanag | tggctnattc | tnaaagctgg | agtctaaatt g | gacnacnac 300 |
| ctntgtattt | actgttggan | ttttgatgct | gcatgacaga | ttttgcttan t | gtaaaaatn 360 |
| aagttcaaga | aaattatgtt | agttttggcc | attat | | 395 |

<210> SEQ ID NO 16
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 16

| | | | | | |
|---|---|---|---|---|---|
| ccaccactaa | aatcctggct | gagccctacn | agtacctgtg | cccctccccc a | ggacgagat 60 |
| nagggcacac | cctttaagtn | aggtgacagg | tcacctttaa | gtgaggacag t | cagctnaat 120 |
| ttcacctctt | gggcttgagt | acctggttct | cgtgccctga | ggcgacnctn a | gccctgcag 180 |
| ctnccatgta | cgtgctgcca | atngtcttga | tcttctccac | gccnctnaac t | tgggcttca 240 |
| gtaggagctg | caggcnagaa | ngaagcggtt | aacagcgcca | ctccatagcc g | cagccnggc 300 |
| tgcccctgct | tctcaaggag | gggtgtgggg | ttcctccacc | atcgccgccc t | tgcaaacac 360 |
| ntctcanggc | ttccctnccg | gctnancgca | ngacttaagc | atgg | 404 |

<210> SEQ ID NO 17
<211> LENGTH: 360
<212> TYPE: DNA
<213> ORGANISM: Homo sapien
<220> FEATURE:
<221> NAME/KEY: misc_feature
<222> LOCATION: (1)...(360)
<223> OTHER INFORMATION: n = A,T,C or G

<400> SEQUENCE: 17

| | | | | | |
|---|---|---|---|---|---|
| ggccagaagc | tttccacaaa | ccagtgaagg | tggcagcaaa | gaaagcctct t | agacnagga 60 |
| gctggcagca | gctgctatct | ngatngacng | cagaaaccaa | ccactaattc a | gcaaacaca 120 |
| acctcatacc | tnaccgcttc | cctttnaatg | gccttcggtg | tgtgcgcaca t | gggcacgtg 180 |
| cggggagaac | catacttatt | cccctnttcc | cggcctacca | cctctnctcc c | ccttctctt 240 |
| ctctncaatt | actntctccn | ctgctttntt | ctnancacta | ctgctngtnt c | nanagccng 300 |
| cccgcaatta | cctggcaaaa | ctcgcgaccc | ttcgggcagc | gctaaanaat g | cacatttac 360 |

<210> SEQ ID NO 18
<211> LENGTH: 316

```
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 18
atacatatac acatatatga ttttagatag agccatatac ctngaagtag t anatttgtt      60 tgtgtgtata tgtatgtgtc tactcatttt aaataaactt gtgatagaga t gtaattntg    120 agccagtttt tcatttgctt aaatnactca ccaagtaact aattaagttn t ctttactct    180 taatgttnag tagtgagatt ctgttgaagg tgatattaaa aaccattcta t attaattaa    240 cattcatgtt gtttttttaaa agcttatttg aaatcnaatt atgattattt t tcataccag    300 tcgatnttat gtangt                                                     316

<210> SEQ ID NO 19
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 19
aagggatgca nataatgctg tgtatgagct tgatggaaaa gaactctgta g tgaaagggt     60 tactattgaa catgctnggg ctcggtcacg aggtggaaga ggtagaggac g atactctga   120 ccgttttagt agtcgcagac ctcgaaatga tagacgaaat gctccacctg t aagaacaga   180 anatcgtctt atagttgaga atttatcctc aagagtcagc tggcaggttt g ttganatac   240 agttttgagt tnttttgatg tggcttttta aaaaagttat gggttactna t gttatattg   300 ttttattaaa agtagttttn aattaatgga tntgatggaa ttgttgtttt             350

<210> SEQ ID NO 20
<211> LENGTH: 367
<212> TYPE: DNA
<213> ORGANISM: Homo sapien
<220> FEATURE:
<221> NAME/KEY: misc_feature
<222> LOCATION: (1)...(367)
<223> OTHER INFORMATION: n = A,T,C or G

<400> SEQUENCE: 20
gntnnncnca agatcctnct ntccccngg gcngcccnc cnccngtnat n accggtttn       60 ntaanatcnn gccgcncccg aagtctcnct nntgccgaga tgncccttat n cncnnatgn   120 ncaattntga cctnnggcga anaatggcng nngtgtatca gtntccnctc t gnggnctct   180 tagnatctga ccactangac ccnctatcct ctcaaaccct gtanncngcc c taatttgtg   240 ccaattagtg catgntanag cntcctggcc cagatggcnt ccatatcctg g tncggcttc   300 cgcccctacc angncatccn catctactag agcttatccg ctncntgngg c gcaccggnt   360 ccccnct                                                               367

<210> SEQ ID NO 21
<211> LENGTH: 366
<212> TYPE: DNA
<213> ORGANISM: Homo sapien
<220> FEATURE:
<221> NAME/KEY: misc_feature
<222> LOCATION: (1)...(366)
```

<223> OTHER INFORMATION: n = A,T,C or G

<400> SEQUENCE: 21

| cccaacacaa | tggtctaagt | anaactgtat | tgctctgtag | tatagttcca | c attggcaac | 60 |
| ctacaatggg | aaaatccata | cataagtcag | ttacttcctn | atgagctttc | t ccttctgaa | 120 |
| tcctttatct | tctgaagaaa | gtacacacct | tggtnatgat | atctttgaat | t gcccttctt | 180 |
| tccaggcatc | agttggatga | ttcatcatgg | taattatggc | attatcatat | t cttcatact | 240 |
| tgtcatacga | aaacaccagt | tctgcccnna | gatgagcttg | ttctgcagct | c ttagcacct | 300 |
| tgggaatatt | cactctagac | cagaaacagc | tcccggtgct | ccctcatttt | c tgaggctta | 360 |
| aatttn | | | | | | 366 |

<210> SEQ ID NO 22
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 22

| acttaatgca | atctctggag | gataatttgg | atcaagaaat | aaagaanaaa | t gaattagga | 60 |
| gaagaaatna | ctgggtnata | tttcaatatt | ttagaacttt | aanaatgttg | a ctatgattt | 120 |
| caatatattt | gtnaaaactg | agatacangt | ttgacctata | tctgcatttt | g ataattaaa | 180 |
| cnaatnnatt | ctatttnaat | gttgtttcag | agtcacagca | cagactgaaa | c ttttttga  | 240 |
| atacctnaat | atcacacttn | tncttnnaat | gatgttgaag | acaatgatga | c atgccttna | 300 |
| gcatataatg | tcgac | | | | | 315 |

<210> SEQ ID NO 23
<211> LENGTH: 202
<212> TYPE: DNA
<213> ORGANISM: Homo sapien
<220> FEATURE:
<221> NAME/KEY: misc_feature
<222> LOCATION: (1)...(202)
<223> OTHER INFORMATION: n = A,T,C or G

<400> SEQUENCE: 23

| actaatccag | tgtggtgnaa | ttccattgtg | ttgggcaact | caggatatta | a atttatnat | 60 |
| ttaaaaattc | ccaagagaaa | naaactccag | gccctgattg | tttcactggg | g aattttacc | 120 |
| aaatgttnca | nnaaganatg | acgctgattc | tgtnaaatct | ttttcagaag | a tagaggaga | 180 |
| acacccaccg | nttcatttta | tg | | | | 202 |

<210> SEQ ID NO 24
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 24

| ggatttcttg | ccctttctc  | ccttttaag  | tatcaatgta | tgaaatccac | c tgtaccacc | 60 |
| ctttctgcca | tacaaccgct | accacatctg | gctcctagaa | cctgttttgc | t ttcatagat | 120 |
| ggatctcgga | accnagtgtt | nacttcattt | ttaaacccca | ttttagcaga | t ngtttgctn | 180 |

```
tggtctgtct gtattcacca tggggcctgt acacaccacg tgtggttata g tcaaacaca    240 gtgccctcca ttgtggccac atgggagacc catnacccna tactgcatcc t gggctgatn    300 acggcactgc atctnacccg acntgggatt gaacccgggg tgggcagcng a attgaacag    360 gatca                                                                  365
```

<210> SEQ ID NO 25
<211> LENGTH: 359
<212> TYPE: DNA
<213> ORGANISM: Homo sapien
<220> FEATURE:
<221> NAME/KEY: misc_feature
<222> LOCATION: (1)...(359)
<223> OTHER INFORMATION: n = A,T,C or G

<400> SEQUENCE: 25

```
gtttcctgct tcaacagtgc ttggacggaa cccggcgctc gttccccacc c cggccggcc    60 gcccatagcc agccctccgt cacctcttca ccgcaccctc ggactgcccc a aggcccccg    120 ccgccnctcc ngcgccncgc agccaccgcc gccnccncca cctctccttn g tccgccnt    180 nacaacgcgt ccacctcgca ngttcgccng aactaccacc nggactcata n gccgccctc    240 aaccgcccga tcaacctgga gctctncccc ccgacnttaa cctttccntg t cttacttac    300 nttaaccgcc gnttattttg cttnaaaaga acttttcccc aatactttct t tcaccnnt    359
```

<210> SEQ ID NO 26
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 26

```
agtgaaacag tatatgtgaa aaggagtttg tgannagcta cataaaaata t tagatatct    60 ttataatttc caataggata ctcatcagtt ttgaataana gacatattct a gagaaacca   120 ggtttctggt ttcagatttg aactctcaag agcttggaag ttatcactcc c atcctcacg   180 acnacnaana aatctnaacn aacngaaanc caatgacttt tcttagatct g tcaaagaac   240 ttcagccacg aggaaaacta tcnccctnaa tactggggac tggaaagaga g ggtacagag   300 aatcacagtg aatcatagcc caagatcagc ttgcccggag ctnaagctng t acgatnatt   360 acttacaggg accacttcac agtnngtnga tnaantgccn                          400
```

<210> SEQ ID NO 27
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 27

```
gaatttctta gaaactgaag tttactctgt tccaagatat atcttcactg t cttaatcaa    60 agggcgctng aatcatagca aatattctca tctttcaact aactttaagt a gttntcctg   120 gaattttaca ttttccagaa aacactcctt tctgtatctg tgaaagaaag t gtgcctcag   180 gctgtagact gggctgcact ggacacctgc gggggactct ggctnagtgn g gacatggtc   240
```

```
agtattgatt tcctcanac tcagcctgtg tagctntgaa agcatggaac a gattacact      300 gcagttnacg tcatcccaca catcttggac tccnagaccc ggggaggtca c atagtccgt     360 tatgna                                                                 366
```

<210> SEQ ID NO 28
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 28

```
agtgggagcc tcctccttcc ccactcagtt ctttacatcc ccgaggcgca g ctgggcnaa     60 ggaagtggcc agctgcagcg cctcctgcag gcagccaacg ttcttgcctg t ggcctgtgc    120 agacacatcc ttgccaccac ctttaccgtc catcangcct gacacctgct g cacccactc   180 gctngctttt aagccccgat nggctgcatt ctggggact tgacacaggc n cgtgatctt    240 gccagcctca ttgtccaccg tgaagagcat ggcaaaaagt ctgaggggag t gcatcttga   300 anagcttcaa ggcttcattc agggccttng ctnaggcgcc nctctccatc t ccnggaata   360 acnagaggct ggtnngggtn actntcaata aactgcttcg tc                       402
```

<210> SEQ ID NO 29
<211> LENGTH: 175
<212> TYPE: DNA
<213> ORGANISM: Homo sapien

<400> SEQUENCE: 29

```
cggacgggca tgaccggtcc ggtcagctgg gtggccagtt tcagttcttc a gcagaactg    60 tctcccttct tggggccga gggcttcctg gggaagagga tgagtttgga g cggtactcc   120 ttcagccgct gcacgttggt ctgcaggac tccgtggact tgttccgcct c ctcg         175
```

<210> SEQ ID NO 30
<211> LENGTH: 360
<212> TYPE: DNA
<213> ORGANISM: Homo sapien

<400> SEQUENCE: 30

```
ttgtatttct tatgatctct gatgggttct tctcgaaaat gccaagtgga a gactttgtg    60 gcatgctcca gatttaaatc cagctgaggc tccctttgtt ttcagttcca t gtaacaatc   120 tggaaggaaa cttcacggac aggaagactg ctggagaaga gaagcgtgtt a gcccatttg   180 aggtctgggg aatcatgtaa agggtaccca gacctcactt ttagttattt a catcaatga   240 gttctttcag ggaaccaaac ccagaattcg gtgcaaaagc caaacatctt g gtgggattt   300 gataaatgcc ttgggacctg gagtgctggg cttgtgcaca ggaagagcac c agccgctga   360
```

<210> SEQ ID NO 31
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 31

```
acgctctaag cctgtccacg agctcaatag ggaagcctgt gatgactaca g actttgcga    60
```

```
acgctacgcc atggtttatg gatacaatgc tgcctataan cgctacttca g gaagcgccg      120 agggaccnaa tgagactgag ggaagaaaaa aaatctcttt ttttctggag g ctggcacct      180 gattttgtat ccccctgtnn cagcattncn gaaatacata ggcttatata c aatgcttct      240 ttcctgtata ttctcttgtc tggctgcacc ccttnttccc gcccccagat t gataagtaa      300 tgaaagtgca ctgcagtnag ggtcaangga gactcancat atgtgattgt t ccntnataa      360 acttctggtg tgatactttc                                                   380

<210> SEQ ID NO 32
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 32
gtgtatggga gcccctgact cctcacgtgc ctgatctgtg cccttggtcc c aggtcaggc      60 ccacccctg cacctccacc tgccccagcc cctgcctctg ccccaagtgg g gccagctgc      120 cctcacttct ggggtggatg atgtgacctt cctngggggga ctgcgaaagg g acaagggtt   180 ccctgaagtc ttacggtcca acatcaggac caagtcccat ggacatgctg a cagggtccc     240 caggggagac cgtntcanta gggatgtgtg cctggctgtg tacgtgggtg t gcagtgcac    300 gtganaagca cgtggcggct tctggggggcc atgtttgggg aaggaagtgt g cccnccacc   360 cttggagaac ctcagtcccn gtagcccct gccctggcac agcngcatnc a cttcaaggg     420 caccctttgg gggttggggt                                                   440

<210> SEQ ID NO 33
<211> LENGTH: 345
<212> TYPE: DNA
<213> ORGANISM: Homo sapien
<220> FEATURE:
<221> NAME/KEY: misc_feature
<222> LOCATION: (1)...(345)
<223> OTHER INFORMATION: n = A,T,C or G

<400> SEQUENCE: 33
tattttaaca atgtttatta ttcatttatc cctctataga accaccaccc a caccgagga    60 gattatttgg agtgggtccc aacctagggc ctggactctg aaatctaact c cccacttcc    120 ctcattttgt gacttaggtg ggggcatggt tcagtcagaa ctggtgtctc c tattggatc   180 gtgcagaagg aggacctagg cacacacata tggtggccac acccaggagg g ttgattggc   240 aggctggaag acaaaagtct cccaataaag gcacttttac ctcaaagang g ggtgggagt   300 tggtctgctg ggaatgttgt tgttggggtg gggaagantt atttc                      345

<210> SEQ ID NO 34
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 34
tgtaattttt ttattggaaa acaaatatac aacttggaat ggattttgag g caaattgtg     60
```

| | |
|---|---|
| ccataagcag attttaagtg gctaaacaaa gtttaaaaag caagtaacaa t aaaagaaaa | 120 |
| tgtttctggt acaggaccag cagtacaaaa aaatagtgta cgagtacctg g ataatacac | 180 |
| ccgttttgca atagtgcaac ttttaagtac atattgttga ctgtccatag t ccacgcaga | 240 |
| gttacaactc cacacttcaa caacaacatg ctgacagttc ctaaagaaaa c tactttaaa | 300 |
| aaaggcataa cccagatgtt ccctcatttg accaactcca tctnagttta g atgtgcaga | 360 |
| agggcttana ttttcccaga gtaagccnca tgcaacatgt tacttgatca a ttttctaaa | 420 |
| ataaggtttt aggacaatga | 440 |

<210> SEQ ID NO 35
<211> LENGTH: 540
<212> TYPE: DNA
<213> ORGANISM: Homo sapien
<220> FEATURE:
<221> NAME/KEY: misc_feature
<222> LOCATION: (1)...(540)
<223> OTHER INFORMATION: n = A,T,C or G

<400> SEQUENCE: 35

| | |
|---|---|
| atagatggaa tttattaagc ttttcacatg tgatagcaca tagttttaat t gcatccaaa | 60 |
| gtactaacaa aaactctagc aatcaagaat ggcagcatgt tatttataa c aatcaacac | 120 |
| ctgtggcttt taaaatttgg ttttcataag ataatttata ctgaagtaaa t ctagccatg | 180 |
| cttttaaaaa atgctttagg tcactccaag cttggcagtt aacatttggc a taaacaata | 240 |
| ataaaacaat cacaatttaa taataacaa atacaacatt gtaggccata a tcatataca | 300 |
| gtataaggga aaaggtggta gtgttganta agcagttatt agaatagaat a ccttggcct | 360 |
| ctatgcaaat atgtctagac actttgattc actcagccct gacattcagt t ttcaaagtt | 420 |
| aggaaacagg ttctacagta tcattttaca gtttccaaca cattgaaaac a agtagaaaa | 480 |
| tgatganttg atttttatta atgcattaca tcctcaagan ttatcaccaa c ccctcaggt | 540 |

<210> SEQ ID NO 36
<211> LENGTH: 555
<212> TYPE: DNA
<213> ORGANISM: Homo sapien
<220> FEATURE:
<221> NAME/KEY: misc_feature
<222> LOCATION: (1)...(555)
<223> OTHER INFORMATION: n = A,T,C or G

<400> SEQUENCE: 36

| | |
|---|---|
| cttcgtgtgc ttgaaaattg gagcctgccc ctcggcccat aagcccttgt t gggaactga | 60 |
| gaagtgtata tggggcccaa nctactggtg ccagaacaca gagacagcag c ccantgcaa | 120 |
| tgctgtcgag cattgcaaac gccatgtgtg gaactaggag gaggaatatt c catcttggc | 180 |
| agaaaccaca gcattggttt ttttctactt gtgtgtctgg gggaatgaac g cacagatct | 240 |
| gtttgacttt gttataaaaa tagggctccc ccacctcccc cntttctgtg t nctttattg | 300 |
| tagcantgct gtctgcaagg gagcccctan ccctggcag acananctgc t tcagtgccc | 360 |
| cttttcctctc tgctaaatgg atgttgatgc actggaggtc ttttancctg c ccttgcatg | 420 |
| gcncctgctg gaggaagana aaactctgct ggcatgaccc acagtttctt g actggangc | 480 |
| cntcaaccct cttggttgaa gccttgttct gaccctgaca tntgcttggg c nctgggtng | 540 |
| gnctgggctt ctnaa | 555 |

<210> SEQ ID NO 37
<211> LENGTH: 280

-continued

```
<212> TYPE: DNA
<213> ORGANISM: Homo sapien
<220> FEATURE:
<221> NAME/KEY: misc_feature
<222> LOCATION: (1)...(280)
<223> OTHER INFORMATION: n = A,T,C or G

<400> SEQUENCE: 37
ccaccgacta taagaactat gccctcgtgt attcctgtac ctgcatcatc c aacttttc      60 acgtggattt tgcttggatc ttggcaagaa accctaatct ccctccagaa a cagtggact    120 ctctaaaaaa tatcctgact tctaataaca ttgatntcaa gaaatgacg g tcacagacc     180 aggtgaactg ccccnagctc tcgtaaccag gttctacagg gaggctgcac c cactccatg   240 ttncttctgc ttcgctttcc cctacccac ccccgccat                             280

<210> SEQ ID NO 38
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 38
catcgagctg gttgtcttct tgcctgccct gtgtcgtaaa atgggggtcc c ttactgcat    60 tatcaaggga aaggcaagac tgggacgtct agtccacagg aagacctgca c cactgtcgc  120 cttcacacag gtgaactcgg aagacaaagg cgctttggct nagctggtgn a agctatcag  180 gaccaattac aatgacngat acgatnagat ccgccntcac tggggtagca a tgtcctggg  240 tcctaagtct gtggctcgta tcgccnagct cgaanaggcn aangctaaag a acttgccac  300 taa                                                                   303

<210> SEQ ID NO 39
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 39
gactcagcgg ctggtgctct tcctgtgcac aagcccagca ctccaggtcc c aaggcattt    60 atcaaatccc accaagatnt ttggcttttg caccgaattc tgggtttggt t ccctnaaag  120 aactcattga tgtaaatnac tnaaagtgag gtctgggtac cctttacatg a ttccccaga  180 cctcanatgg gctaacacgc ttctcttctc cagcagtctt cctntccgtg a agttacctt  240 ccagattgtt acatggaact gaanacaaag ggagcctcag ctngatttaa a tctggagca  300

<210> SEQ ID NO 40
<211> LENGTH: 318
<212> TYPE: DNA
<213> ORGANISM: Homo sapien
<220> FEATURE:
<221> NAME/KEY: misc_feature
<222> LOCATION: (1)...(318)
<223> OTHER INFORMATION: n = A,T,C or G

<400> SEQUENCE: 40
cccaacacaa tggctgagga caaatcagtt ctctgtgacc agacatgaga a ggttgccaa    60
```
tgggctgttg ggcgaccaag gccttccgg agtcttcgtc ctctatgagc t ctcgcccat       120 gatggtgaag ctgacggaga agcacaggtc cttcacccac ttcctgacag g tgtgtgcgc       180 catcattggg ggcatgttca cagtggctgg actcatcgat tcgctcatct a ccactcagc       240 acgagccatc cagaaaaaaa ttgatctngg gaagacnacg tagtcaccct c ggtncttcc      300 tctgtctcct ctttctcc                                                      318

<210> SEQ ID NO 41
<211> LENGTH: 302
<212> TYPE: DNA
<213> ORGANISM: Homo sapien
<220> FEATURE:
<221> NAME/KEY: misc_feature
<222> LOCATION: (1)...(302)
<223> OTHER INFORMATION: n = A,T,C or G

<400> SEQUENCE: 41
acttagatgg ggtccgttca ggggatacca gcgttcacat ttttccttttt a agaaagggt       60 cttggcctga atgttcccca tccggacaca ggctgcatgt ctctgtnagt g tcaaagctg      120 ccatnaccat ctcggtaacc tactcttact ccacaatgtc tatnttcact g cagggctct      180 ataatnagtc cataatgtaa atgcctggcc caagacntat ggcctgagtt t atccnaggc      240 ccaaacnatt accagacatt cctcttanat tgaaaacgga tntctttccc t tggcaaaga      300 tc                                                                       302

<210> SEQ ID NO 42
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 42
cttaataagt ttaaggccaa ggcccgttcc attcttctag caactgacgt t gccagccga       60 ggtttggaca tacctcatgt aaatgtggtt gtcaactttg acattcctac c cattccaag      120 gattacatcc atcgagtagg tcgaacagct agagctgggc gctccggaaa g gctattact      180 tttgtcacac agtatgatgt ggaactcttc cagcgcatag aacactttat t gggaagaaa      240 ctaccaggtt ttccaacaca ggatgatgag gttatgatgc tnacggaacg c gtcgctna      299

<210> SEQ ID NO 43
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 43
ccaacaatgt caagacagcc gtctgtgaca tcccacctcg tggcctcaan a tggcagtca       60 ccttcattgg caatagcaca gccntccggg agctcttcaa gcgcatctcg g agcagttca     120 ctgccatgtt ccgccggaag gccttcctcc actggtacac aggcgagggc a tggacaaga     180 tggagttcac cgaggctgag agcaacatga acgacctcgt ctctnagtat c agcagtacc     240 gggatgccac cgcagaaaana ggaggaggat ttcggtnagg aggccgaaga a ggaggcctg     300 aggca                                                                    305

<210> SEQ ID NO 44
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 44

| | | | | | |
|---|---|---|---|---|---|
| tttctgtggg | ggaaacctga | tctcgacnaa | attagagaat | tttgtcagcg g | tatttcggc 60 |
| tggaacagaa | cgaaaacnga | tnaatctctg | tttcctgtat | taaagcaact c | gatncccag 120 |
| cagacacagc | tccnaattga | ttccttcttt | ngattagcac | aacagggaga a | agaanatgc 180 |
| ttaacgtatt | aagagccnga | gactaaacag | agctttgaca | tgtatgctta g | gaaagagaa 240 |
| agaagcagcn | gcccgcgnaa | ttngaagcng | tttctgttgc | cntgganaaa g | aatttgagc 300 |
| ttctttatta | ggccaacgaa | aaaccccgaa | ananaggcnt | tacnatacct t | ngaaaantc 360 |
| tccngccnna | aaaagaaaga | agctttcnga | ttcttaacc | | 399 |

<210> SEQ ID NO 45
<211> LENGTH: 440
<212> TYPE: DNA
<213> ORGANISM: Homo sapien
<220> FEATURE:
<221> NAME/KEY: misc_feature
<222> LOCATION: (1)...(440)
<223> OTHER INFORMATION: n = A,T,C or G

<400> SEQUENCE: 45

| | | | | | |
|---|---|---|---|---|---|
| gcgggagcag | aagctaaagc | caaagcccaa | gagagtggca | gtgccagcac t | ggtgccagt 60 |
| accagtacca | ataacagtgc | cagtgccagt | gccagcacca | gtggtggctt c | agtgctggt 120 |
| gccagcctga | ccgccactct | cacatttggg | ctcttcgctg | gccttggtgg a | gctggtgcc 180 |
| agcaccagtg | gcagctctgg | tgcctgtggt | ttctcctaca | agtgagattt t | aggtatctg 240 |
| ccttggtttc | agtggggaca | tctggggctt | anggggcngg | gataaggagc t | ggatgattc 300 |
| taggaaggcc | cangttggag | aangatgtgn | aangtgtgcc | aagacactgc t | tttggcatt 360 |
| ttattccttt | ctgtttgctg | gangtcaatt | gacccttnna | ntttctctta c | ttgtgtttt 420 |
| canatatngt | taatcctgcc | | | | 440 |

<210> SEQ ID NO 46
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 46

| | | | | | |
|---|---|---|---|---|---|
| gctctgtaat | ttcacatttt | aaaccttccc | ttgacctcac | attcctcttc g | gccacctct 60 |
| gtttctctgt | tcctcttcac | agcaaaaact | gttcaaaaga | gttgttgatt a | ctttcattt 120 |
| ccactttctc | acccccattc | tccctcaat | taactctcct | tcatcccat g | atgccatta 180 |
| tgtggctntt | attanagtca | ccaaccttat | tctccaaaac | anaagcaaca a | ggactttga 240 |
| cttctcagca | gcactcagct | ctggtncttg | aaacacccc | gttacttgct a | ttcctccta 300 |
| cctcataaca | atctccttcc | cagcctctac | tgctgccttc | tctgagttct t | cccagggtc 360 |

```
ctaggctcag atgtagtgta gctcaaccct gctacacaaa gnaatctcct g aaagcctgt        420 aaaaatgtcc atncntgtcc tgtgagtgat ctnccangna naataacaaa t t                472
```

<210> SEQ ID NO 47
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 47

```
ccttcctccg cctggccatc cccagcatgc tcatgctgtg catggagtgg t gggcctatg        60 aggtcgggag cttcctcagt ggtctgtatg aggatggatg acggggactg g tgggaacct       120 gggggccctg tctgggtgca aggcgacagc tgtctttctt caccaggcat c ctcggcatg       180 gtggagctgg gcgctcagtc catcgtgtat gaactggcca tcattgtgta c atggtccct      240 gcaggcttca gtgtggctgc cagtgtccgg gtangaaacg ctctgggtgc t ggagacatg       300 gaagcaggca cggaagtcct ctaccgtttc cctgctgatt acagtgctct t tgctgtanc      360 cttcagtgtc ctgctgttaa gctgtaagga tcacntgggg tacatttttta c taccgaccg     420 agaacatcat taatctggtg gctcaggtgg ttccaattta tgctgtttcc c acctctttg     480 aagctcttgc tgctcaggta cacgccaatt ttgaaaagta acaacgtgc c tcggagtgg       540 gaattctgct                                                              550
```

<210> SEQ ID NO 48
<211> LENGTH: 214
<212> TYPE: DNA
<213> ORGANISM: Homo sapien
<220> FEATURE:
<221> NAME/KEY: misc_feature
<222> LOCATION: (1)...(214)
<223> OTHER INFORMATION: n = A,T,C or G

<400> SEQUENCE: 48

```
agaaggacat aaacaagctg aacctgccca agacgtgtga tatcagcttc t cagatccag       60 acaacctcct caacttcaag ctggtcatct gtcctgatna gggcttctac n agagtggga     120 agtttgtgtt cagttttaag gtgggccagg gttacccgca tgatcccccc a aggtgaagt     180 gtgagacnat ggtctatcac cccnacattg acct                                   214
```

<210> SEQ ID NO 49
<211> LENGTH: 267
<212> TYPE: DNA
<213> ORGANISM: Homo sapien
<220> FEATURE:
<221> NAME/KEY: misc_feature
<222> LOCATION: (1)...(267)
<223> OTHER INFORMATION: n = A,T,C or G

<400> SEQUENCE: 49

```
atctgcctaa aatttattca aataatgaaa atnaatctgt tttaagaaat t cagtctttt       60 agtttttagg acaactatgc acaaatgtac gatggagaat tcttttttgga t naactctag    120 gtngaggaac ttaatccaac cggagctntt gtgaaggtca gaanacagga g agggaatct     180 tggcaaggaa tggagacnga gtttgcaaat tgcagctaga gtnaatngtt n taaatggga    240 ctgctnttgt gtctcccang gaaagtt                                           267
```

```
<210> SEQ ID NO 50
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 50
gactgggtca aagctgcatg aaaccaggcc ctggcagcaa cctgggaatg g ctggaggtg      60 ggagagaacc tgacttctct ttccctctcc ctcctccaac attactggaa c tctgtcctg     120 ttgggatctt ctgagcttgt ttccctgctg ggtgggacag aggacaaagg a gaagggagg     180 gtctagaaga ggcagccctt ctttgtcctc tggggtnaat gagcttgacc t anagtagat    240 ggagagacca anagcctctg atttttaatt tccataanat gttcnaagta t atntntacc    300

<210> SEQ ID NO 51
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 51
gggtaaaatc ctgcagcacc cactctggaa aatactgctc ttaattttcc t gaaggtggc      60 cccctatttc tagttggtcc aggattaggg atgtgggta tagggcattt a aatcctctc     120 aagcgctctc caagcacccc cggcctgggg gtnagtttct catcccgcta c tgctgctgg    180 gatcaggttn aataaatgga actcttcctg tctggcctcc aaagcagcct a aaaactgag    240 gggctctgtt agaggggacc tccaccctnn ggaagtccga ggggctnggg a agggtttct    300

<210> SEQ ID NO 52
<211> LENGTH: 267
<212> TYPE: DNA
<213> ORGANISM: Homo sapien
<220> FEATURE:
<221> NAME/KEY: misc_feature
<222> LOCATION: (1)...(267)
<223> OTHER INFORMATION: n = A,T,C or G

<400> SEQUENCE: 52
aaaatcaact tcntgcatta atanacanat tctanancag gaagtgaana t aattttctg      60 cacctatcaa ggaacnnact tgattgcctc tattnaacan atatatcgag t tnctatact   120 tacctgaata ccnccgcata actctcaacc nanatncntc nccatgacac t cnttcttna    180 atgctantcc cgaattcttc attatatcng tgatgttcgn cctgntnata t atcagcaag    240 gtatgtnccn taactgccga nncaang                                          267

<210> SEQ ID NO 53
<211> LENGTH: 401
<212> TYPE: DNA
<213> ORGANISM: Homo sapien

<400> SEQUENCE: 53
agsctttagc atcatgtaga agcaaactgc acctatggct gagataggtg c aatgaccta     60 caagattttg tgttttctag ctgtccagga aaagccatct tcagtcttgc t gacagtcaa   120 agagcaagtg aaaccatttc cagcctaaac tacataaaag cagccgaacc a atgattaaa   180
```

```
gacctctaag gctccataat catcattaaa tatgcccaaa ctcattgtga c tttttattt      240 tatatacagg attaaaatca acattaaatc atcttattta catggccatc g gtgctgaaa      300 ttgagcattt taaatagtac agtaggctgg tatacattag gaaatggact g cactggagg      360 caaatagaaa actaaagaaa ttagataggc tggaaatgct t                           401

<210> SEQ ID NO 54
<211> LENGTH: 401
<212> TYPE: DNA
<213> ORGANISM: Homo sapien

<400> SEQUENCE: 54
cccaacacaa tggataaaaa cacttatagt aaatggggac attcactata a tgatctaag       60 aagctacaga ttgtcatagt tgttttcctg ctttacaaaa ttgctccaga t ctggaatgc      120 cagtttgacc tttgtcttct ataatatttc cttttttttcc cctctttgaa t ctctgtata     180 tttgattctt aactaaaatt gttctcttaa atattctgaa tcctggtaat t aaaagtttg      240 ggtgtatttt ctttacctcc aaggaaagaa ctactagcta caaaaaatat t ttggaataa      300 gcattgtttt ggtataaggt acatattttg gttgaagaca ccagactgaa g taaacagct      360 gtgcatccaa tttattatag ttttgtaagt aacaatatgt a                           401

<210> SEQ ID NO 55
<211> LENGTH: 933
<212> TYPE: DNA
<213> ORGANISM: Homo sapien

<400> SEQUENCE: 55
tttactgctt ggcaaagtac cctgagcatc agcagagatg ccgagatgaa a tcagggaac       60 tcctagggga tgggtcttct attacctggg aacacctgag ccagatgcct t acaccacga     120 tgtgcatcaa ggaatgcctc cgcctctacg caccggtagt aaactatccc g gttactcga     180 caaacccatc acctttccag atggacgctc cttacctgca ggaataactg t gtttatcaa     240 tatttgggct cttcaccaca accctatttt ctgggaagac cctcaggtct t taaccccctt    300 gagattctcc agggaaaatt ctgaaaaaat acatccctat gccttcatac c attctcagc     360 tggattaagg aactgcattg gcagcatttt tgccataatt gagtgtaaag t ggcagtggc     420 attaactctg ctccgcttca agctggctcc agaccactca aggccaccca g ctgtcgtca     480 agttgcctca agtccaagaa tggaatccat gtgtttgcaa aaaaagtttg c taattttaa     540 gtccttttcg tataagaatt aakgagacaa ttttcctacc aaaggaagaa c aaaaggata     600 aatataatac aaaatatatg tatatggttg tttgacaaat tatataactt a ggatacttc     660 tgactggttt tgacatccat taacagtaat tttaatttct ttgctgtatc t ggtgaaacc     720 cacaaaaaca cctgaaaaaa ctcaagctga gttccaatgc gaagggaaat g attggtttg     780 ggtaactagt ggtagagtgg ctttcaagca tagtttgatc aaaactccac t cagtatctg     840 cattactttt atctctgcaa atatctgcat gatagcttta ttctcagtta t ctttcccca     900 taataaaaaa tatctgccaa aaaaaaaaaa aaa                                    933

<210> SEQ ID NO 56
<211> LENGTH: 480
<212> TYPE: DNA
<213> ORGANISM: Homo sapien

<400> SEQUENCE: 56
ggctttgaag catttttgtc tgtgctccct gatcttcagg tcaccaccat g aagttctta      60
```

```
gcagtcctgg tactcttggg agtttccatc tttctggtct ctgcccagaa t ccgacaaca    120 gctgctccag ctgacacgta tccagctact ggtcctgctg atgatgaagc c cctgatgct    180 gaaaccactg ctgctgcaac cactgcgacc actgctgctc ctaccactgc a accaccgct    240 gcttctacca ctgctcgtaa agacattcca gttttaccca aatgggttgg g gatctcccg    300 aatggtagag tgtgtccctg agatggaatc agcttgagtc ttctgcaatt g gtcacaact    360 attcatgctt cctgtgattt catccaacta cttaccttgc ctacgatatc c cctttatct    420 ctaatcagtt tattttcttt caaataaaaa ataactatga gcaacaaaaa a aaaaaaaaa    480
```

<210> SEQ ID NO 57
<211> LENGTH: 798
<212> TYPE: DNA
<213> ORGANISM: Homo sapien

<400> SEQUENCE: 57

```
agcctacctg gaaagccaac cagtcctcat aatggacaag atccaccagc t cctcctgtg     60 gactaacttt gtgatatggg aagtgaaaat agttaacacc ttgcacgacc a aacgaacga    120 agatgaccag agtactctta accccttaga actgttttte cttttgtatc t gcaatatgg    180 gatggtattg ttttcatgag cttctagaaa tttcacttgc aagtttattt t tgcttcctg    240 tgttactgcc attcctattt acagtatatt tgagtgaatg attatatttt t aaaaagtta    300 catggggctt ttttggttgt cctaaactta caaacattcc actcattctg t ttgtaactg    360 tgattataat ttttgtgata atttctggcc tgattgaagg aaatttgaga g gtctgcatt    420 tatatatttt aaatagattt gataggtttt taaattgctt tttttcataa g gtatttata    480 aagttatttg gggttgtctg ggattgtgtg aaagaaaatt agaaccccgc t gtatttaca    540 tttaccttgg tagtttatttt gtggatggca gttttctgta gttttgggga c tgtggtagc    600 tcttggattg ttttgcaaat tacagctgaa atctgtgtca tggattaaac t ggcttatgt    660 ggctagaata ggaagagaga aaaaatgaaa tggttgttta ctaattttat a ctcccatta    720 aaaatttta atgttaagaa aaccttaaat aaacatgatt gatcaatatg g aaaaaaaa     780 aaaaaaaaaa aaaaaaaa                                                    798
```

<210> SEQ ID NO 58
<211> LENGTH: 280
<212> TYPE: DNA
<213> ORGANISM: Homo sapien

<400> SEQUENCE: 58

```
ggggcagctc ctgaccctcc acagccacct ggtcagccac cagctggggc a acgagggtg     60 gaggtcccac tgagcctctc gcctgccccc gccactcgtc tggtgcttgt t gatccaagt    120 cccctgcctg gtcccccaca aggactccca tccaggcccc ctctgccctg c cccttgtca    180 tggaccatgg tcgtgaggaa gggctcatgc cccttattta tgggaaccat t tcattctaa    240 cagaataaac cgagaaggaa accagaaaaa aaaaaaaaa                             280
```

<210> SEQ ID NO 59
<211> LENGTH: 382
<212> TYPE: DNA
<213> ORGANISM: Homo sapien

<400> SEQUENCE: 59

```
aggcgggagc agaagctaaa gccaaagccc aagagagtgg cagtgccagc a ctggtgcca     60
```

```
gtaccagtac caataacagt gccagtgcca gtgccagcac cagtggtggc t tcagtgctg      120 gtgccagcct gaccgccact ctcacatttg ggctcttcgc tggccttggt g gagctggtg      180 ccagcaccag tggcagctct ggtgcctgtg gtttctccta caagtgagat t ttagatatt      240 gttaatcctg ccagtctttc tcttcaagcc agggtgcatc ctcagaaacc t actcaacac      300 agcactctag gcagccacta tcaatcaatt gaagttgaca ctctgcatta a atctatttg      360 ccattaaaaa aaaaaaaaaa aa                                                382

<210> SEQ ID NO 60
<211> LENGTH: 602
<212> TYPE: DNA
<213> ORGANISM: Homo sapien

<400> SEQUENCE: 60
tgaagagccg cgcggtggag ctgctgcccg atgggactgc caaccttgcc a agctgcagc       60 ttgtggtgga gaatagtgcc cagcgggtca tccacttggc gggtcagtgg g agaagcacc      120 gggtcccatc ctcgtgagta ccgccactcc gaaagctgca ggattgcaga g agctggaat      180 cttctcgacg gctggcagag atccaagaac tgcaccagag tgtccgggcg g ctgctgaag      240 aggcccgcag gaaggaggag gtctataagc agctgatgtc agagctggag a ctctgccca      300 gagatgtgtc ccggctggcc tacacccagc gcatcctgga gatcgtgggc a acatccgga      360 agcagaagga agagatcacc aagatcttgt ctgatacgaa ggagcttcag a aggaaatca      420 actccctatc tgggaagctg gaccggacgt ttgcggtgac tgatgagctt g tgttcaagg      480 atgccaagaa ggacgatgct gttcggaagg cctataagta tctagctgct c tgcacgaga      540 actgcagcca gctcatccag accatcgagg acacaggcac catcatgcgg g aggttcgag      600 ac                                                                      602

<210> SEQ ID NO 61
<211> LENGTH: 1368
<212> TYPE: DNA
<213> ORGANISM: Homo sapien
<220> FEATURE:
<221> NAME/KEY: misc_feature
<222> LOCATION: (1)...(1368)
<223> OTHER INFORMATION: n = A,T,C or G

<400> SEQUENCE: 61
ccagtgagcg cgcgtaatac gactcactat agggcgaatt gggtaccggg c cccccctcg       60 agcggccgcc cttttttttt tttttttatt gatcagaatt caggctttat t attgagcaa      120 tgaaaacagc taaaacttaa ttccaagcat gtgtagttaa agtttgcaaa g tgggatatt      180 gttcacaaaa cacattcaat gtttaaacac tatttatttg aagaacaaaa t atatttaaa      240 attgtttgct tctaaaaagc ccatttccct ccaagtctaa actttgtaat t tgatattaa      300 gcaatgaagt tattttgtac aatctagtta acaagcaga atagcactag g cagaataaa       360 aaattgcaca gacgtatgca attttccaag atagcattct ttaaattcag t tttcagctt      420 ccaaagattg gttgcccata atagacttaa acatataatg atggctaaaa a aaataagta      480 tacgaaaatg taaaaaagga aatgtaagtc cactctcaat ctcataaaag g tgagagtaa      540 ggatgctaaa gcaaataaa tgtaggttct ttttttctgt ttccgtttat c atgcaatct      600 gcttctttga tatgccttag ggttacccat ttaagttaga ggttgtaatg c aatggtggg      660 aatgaaaatt gatcaaatat acaccttgtc atttcatttc aaattgcggg c tggaaactt      720 ccaaaaaaag ggtaggcatg aagaaaaaaa aaatcmaatc agaacctctt c aggggtttg      780
```

| | |
|---|---|
| kgktctgata tggcagacar gatacaagtc ccaccaggag atggagcaat t caaaataag | 840 |
| ggtaatgggc tgacaaggta ttattgccag catgggacag aatgagcaac a ggctgaaaa | 900 |
| gttttttggat tatatagcac ctagagtctc tgatgtaggg aatttttgtt a gtcaaacat | 960 |
| acgctaaact tccaagggaa aatctttcag gtagcctaag cttgcttttc t agagtgatg | 1020 |
| agttgcattg ctactgtgat tttttgaaaa caaactgggt ttgtacaagt g agaaagact | 1080 |
| agagagaaag attttagtct gtttagcaga agccatttta tctgcgtgca c atggatcaa | 1140 |
| tatttctgat cccctatacc ccaggaaggg caaaatccca aagaaatgtg t tagcaaaat | 1200 |
| tggctgatgc tatcatattg ctatggacat tgatcttgcc caacacaatg g aattccacc | 1260 |
| acactggact agtggatcca ctagttctag agcggccggc caccgcggtg g agctccagc | 1320 |
| ttttgttccc tttagtgagg gttaattgcg cgcttggcgt aatcatnn | 1368 |

<210> SEQ ID NO 62
<211> LENGTH: 924
<212> TYPE: DNA
<213> ORGANISM: Homo sapien
<220> FEATURE:
<221> NAME/KEY: misc_feature
<222> LOCATION: (1)...(924)
<223> OTHER INFORMATION: n = A,T,C or G

<400> SEQUENCE: 62

| | |
|---|---|
| caaaggnaca ggaacagctt gnaaagtact gncatncctn cctgcaggga c cagccctttt | 60 |
| gcctccaaaa gcaataggaa atttaaaaga tttncactga gaagggggncc a cgtttnart | 120 |
| tntnaatgtn tcargnanar tnccttncaa atgncrnctn cactnactnr g natttgggt | 180 |
| tnccgnrtnc mgnactatnt caggtttgaa aaactggatc tgccacttat c agttatgtg | 240 |
| accttaaaga actccgttaa tttctcagag cctcagtttc cttgtctata a gttgggagt | 300 |
| aatattaata ctatcatttt tccaaggatt gatgtgaaca ttaatgaggt g aaatgacag | 360 |
| atgtgtatca tggttcctaa taaacatcca aaatatagta cttactattg t cattattat | 420 |
| tacttgtttg aagctaaaga cctcacaata gaatcccatc cagcccacca g acagagytc | 480 |
| tgagttttct agtttggaag agctattaaa taacaacktc tagtgtcaat t ctatacttg | 540 |
| ttatggtcaa gtaactgggc tcagcatttt acattcattg tctctttaag t tctagcaat | 600 |
| gtgaagcagg aactatgatt atattgacta cataaatgaa gaaattgagg c tcagataca | 660 |
| ttaagtaatt ctcccagggt cacacagcta gaactggcaa agcctgggat t gatccatga | 720 |
| tcttccagca ttgaagaatc ataaatgtaa ataactgcaa ggccttttcc t cagaagagc | 780 |
| tcctggtgct tgcaccaacc cactagcact tgttctctac aggggaacat c tgtgggcct | 840 |
| gggaatcact gcacgtcgca agagatgttg cttctgatga attattgttc c tgtcagtgg | 900 |
| tgtgaaggca aaaaaaaaaa aaaa | 924 |

<210> SEQ ID NO 63
<211> LENGTH: 1079
<212> TYPE: DNA
<213> ORGANISM: Homo sapien

<400> SEQUENCE: 63

| | |
|---|---|
| agtcccaaga actcaataat ctcttatgtt ttcttttgaa gacttatttt a aatattaac | 60 |
| tatttcggtg cctgaatgga aaaatataaa cattagctca gagacaatgg g gtacctgtt | 120 |
| tggaatccag ctggcagcta taagcaccgt tgaaaactct gacaggcttt g tgcccttttt | 180 |

-continued

| | | |
|---|---|---|
| tattaaatgg cctcacatcc tgaatgcagg aatgtgttcg tttaaataaa c attaatctt | 240 |
| taatgttgaa ttctgaaaac acaaccataa atcatagttg gttttctgtg acaatgatc | 300 |
| tagtacatta tttcctccac agcaaaccta cctttccaga aggtggaaat t gtatttgca | 360 |
| acaatcaggg caaaacccac acttgaaaag cattttacaa tattatatct a agttgcaca | 420 |
| gaagacccca gtgatcacta ggaaatctac acagtccag tttttctaat c caagaaggt | 480 |
| caaacttcgg ggaataatgt gtccctcttc tgctgctgct ctgaaaaata t tcgatcaaa | 540 |
| acgaagttta caagcagcag ttattccaag attagagttc atttgtgtat c ccatgtata | 600 |
| ctggcaatgt ttaggtttgc ccaaaaactc ccagacatcc acaatgttgt t gggtaaacc | 660 |
| accacatctg gtaacctctc gatcccttag atttgtatct cctgcaaata t aactgtagc | 720 |
| tgactctgga gcctcttgca ttttctttaa aaccattttt aactgattca t tcgttccgc | 780 |
| agcatgccct ctggtgctct ccaaatggga tgtcataagg caaagctcat t tcctgacac | 840 |
| attcacatgc acacataaaa ggtttctcat cattttggta cttggaaaag g aataatctc | 900 |
| ttggcttttt aatttcactc ttgatttctt caacattata gctgtgaaat a tccttcttc | 960 |
| atgacctgta ataatctcat aattacttga tctcttcttt aggtagctat a atatgggg | 1020 |
| aataacttcc tgtagaaata tcacatctgg gctgtacaaa gctaagtagg a acacaccc | 1079 |

<210> SEQ ID NO 64
<211> LENGTH: 1001
<212> TYPE: DNA
<213> ORGANISM: Homo sapien

<400> SEQUENCE: 64

| | | |
|---|---|---|
| gaatgtgcaa cgatcaagtc agggtatctg tggtatccac cactttgagc a tttatcgat | 60 |
| tctatatgtc aggaacattt caagttatct gttctagcaa ggaaatataa a atacttata | 120 |
| gttaactatg gcctatctac agtgcaacta aaaactagat tttattcctt t ccacctgtg | 180 |
| ggtttgtatt catttaccac cctcttttca ttcccttct cacccacaca c tgtgccggg | 240 |
| cctcaggcat atactattct actgtctgtc tctgtaagga ttatcatttt a gcttccaca | 300 |
| tatgagagaa tgcatgcaaa gttttctctt ccatgtctgg cttatttcac t taacataat | 360 |
| gacctccgct tccatccatg ttatttatat tacccaatag tgttcataaa t atatataca | 420 |
| cacatatata ccacattgca tttgtccaat tattcattga cggaaactgg t taatgttat | 480 |
| atcgttgcta ttgtggatag tgctgcaata aacacgcaag tggggatata a tttgaagag | 540 |
| ttttttttgtt gatgttcctc caaattttaa gattgttttg tctatgtttg t gaaatggc | 600 |
| gttagtattt tcatagagat tgcattgaat ctgtagattg ctttgggtaa g tatggttat | 660 |
| tttgatggta ttaattttt cattccatga agatgagatg tctttccatt g tttgtgtcc | 720 |
| tctacatttt ctttcatcaa agttttgttg tatttttgaa gtagatgtat t tcaccttat | 780 |
| agatcaagtg tattccctaa atattttatt tttgtagcta ttgtagatga a attgccttc | 840 |
| ttgatttctt tttcacttaa ttcattatta gtgtatggaa atgttatgga t ttttatttg | 900 |
| ttggttttta atcaaaaact gtattaaact tagagttttt tgtggagttt t taagttttt | 960 |
| ctagatataa gatcatgaca tctaccaaaa aaaaaaaaa a | 1001 |

<210> SEQ ID NO 65
<211> LENGTH: 575
<212> TYPE: DNA
<213> ORGANISM: Homo sapien

<400> SEQUENCE: 65

-continued

| | | |
|---|---|---|
| acttgatata aaaaggatat ccataatgaa tattttatac tgcatccttt a cattagcca | 60 |
| ctaaatacgt tattgcttga tgaagacctt tcacagaatc ctatggattg c agcatttca | 120 |
| cttggctact tcatacccat gccttaaaga ggggcagttt ctcaaaagca g aaacatgcc | 180 |
| gccagttctc aagttttcct cctaactcca tttgaatgta agggcagctg g cccccaatg | 240 |
| tggggaggtc cgaacatttt ctgaattccc attttcttgt tcgcggctaa a tgacagttt | 300 |
| ctgtcattac ttagattccc gatctttccc aaaggtgttg atttacaaag a ggccagcta | 360 |
| atagccagaa atcatgaccc tgaaagagag atgaaatttc aagctgtgag c caggcagga | 420 |
| gctccagtat ggcaaaggtt cttgagaatc agccatttgg tacaaaaaag a tttttaaag | 480 |
| cttttatgtt ataccatgga gccatagaaa ggctatggat tgtttaagaa c tattttaaa | 540 |
| gtgttccaga cccaaaaagg aaaaaaaaaa aaaaa | 575 |

<210> SEQ ID NO 66
<211> LENGTH: 831
<212> TYPE: DNA
<213> ORGANISM: Homo sapien

<400> SEQUENCE: 66

| | | |
|---|---|---|
| attgggctcc ttctgctaaa cagccacatt gaaatggttt aaaagcaagt c agatcaggt | 60 |
| gatttgtaaa attgtattta tctgtacatg tatgggcttt taattcccac c aagaaagag | 120 |
| agaaattatc ttttttagtta aaaccaaatt tcacttttca aaatatcttc c aacttattt | 180 |
| attggttgtc actcaattgc ctatatatat atatatatat gtgtgtgtgt g tgtgtgcgc | 240 |
| gtgagcgcac gtgtgtgtat gcgtgcgcat gtgtgtgtat gtgtattatc a gacataggt | 300 |
| ttctaacttt tagatagaag aggagcaaca tctatgccaa atactgtgca t tctacaatg | 360 |
| gtgctaatct cagacctaaa tgatactcca tttaatttaa aaaagagttt t aaataatta | 420 |
| tctatgtgcc tgtatttccc ttttgagtgc tgcacaacat gttaacatat t agtgtaaaa | 480 |
| gcagatgaaa caaccacgtg ttctaaagtc tagggattgt gctataatcc c tatttagtt | 540 |
| caaaattaac cagaattctt ccatgtgaaa tggaccaaac tcatattatt g ttatgtaaa | 600 |
| tacagagttt taatgcagta tgacatccca caggggaaaa gaatgtctgt a gtgggtgac | 660 |
| tgttatcaaa tattttatag aatacaatga acggtgaaca gactggtaac t tgtttgagt | 720 |
| tcccatgaca gatttgagac ttgtcaatag caaatcattt ttgtatttaa a tttttgtac | 780 |
| tgatttgaaa aacatcatta aatatcttta aaagtaaaaa aaaaaaaaa a | 831 |

<210> SEQ ID NO 67
<211> LENGTH: 590
<212> TYPE: DNA
<213> ORGANISM: Homo sapien

<400> SEQUENCE: 67

| | | |
|---|---|---|
| gtgctctgtg tattttttta ctgcattaga cattgaatag taatttgcgt t aagatacgc | 60 |
| ttaaaggctc tttgtgacca tgtttccctt tgtagcaata aaatgttttt t acgaaaact | 120 |
| ttctccctgg attagcagtt taaatgaaac agagttcatc aatgaaatga g tatttaaaa | 180 |
| taaaatttg ccttaatgta tcagttcagc tcacaagtat tttaagatga t tgagaagac | 240 |
| ttgaattaaa gaaaaaaaaa ttctcaatca tattttttaaa atataagact a aaattgttt | 300 |
| ttaaaacaca tttcaaatag aagtgagttt gaactgacct tatttatact c tttttaagt | 360 |
| ttgttccttt tccctgtgcc tgtgtcaaat cttcaagtct tgctgaaaat a catttgata | 420 |

-continued

```
caaagttttc tgtagttgtg ttagttcttt tgtcatgtct gtttttggct g aagaaccaa      480 gaagcagact tttcttttaa aagaattatt tctctttcaa atatttctat c cttttttaaa     540 aaattcctttt ttatggctta tatacctaca tatttaaaaa aaaaaaaaaa                590
```

COMPOUNDS FOR IMMUNOTHERAPY OF BREAST CANCER AND METHODS FOR THEIR USE

REFERENCE TO RELATED APPLICATIONS

This application is a continuation-in-part of U.S. patent application Ser. No. 08/998,253, filed Dec. 24, 1997 now abandoned.

TECHNICAL FIELD

The present invention relates generally to compositions and methods for the treatment of breast cancer. The invention is more particularly related to polypeptides comprising at least a portion of a protein that is preferentially expressed in breast tumor tissue and to DNA molecules encoding such polypeptides. Such polypeptides may be used in vaccines and pharmaceutical compositions for treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are now one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for therapy and diagnosis of breast cancer. The present invention fulfills these needs and further provides other related advantages.

SUMMARY OF THE INVENTION

The present invention provides compounds and methods for immunotherapy of breast cancer. In one aspect, isolated polypeptides are provided comprising at least an immunogenic portion of a breast tumor protein or a variant of said protein that differs only in conservative substitutions and/or modifications, wherein the breast tumor protein comprises an amino acid sequence encoded by a DNA molecule having a partial sequence selected from the group consisting of (a) nucleotide sequences recited in SEQ ID NOS: 3, 10, 17, 24, 45–52 and 55–67, (b) complements of said nucleotide sequences and (c) sequences that hybridize to a sequence of (a) or (b) under moderately stringent conditions.

In related aspects, isolated DNA molecules encoding the above polypeptides are provided. In specific embodiments, such DNA molecules have partial sequences provided in SEQ ID NOS: 3, 10, 17, 24, 45–52 and 55–67. The present invention further provides expression vectors comprising the above DNA molecules and host cells transformed, or transfected with such expression vectors. In preferred embodiments, the host cells are selected from the group consisting of *E. coli,* yeast and mammalian cells.

In another aspect, the present invention provides fusion proteins comprising a first and a second inventive polypeptide or, alternatively, an inventive polypeptide and a known breast antigen.

The present invention also provides pharmaceutical compositions comprising at least one of the above polypeptides, or a DNA molecule encoding such a polypeptide, and a physiologically acceptable carrier, together with vaccines comprising at least one or more such polypeptide or DNA molecule in combination with a non-specific immune response enhancer. Pharmaceutical compositions and vaccines comprising one or more of the above fusion proteins are also provided.

In related aspects, pharmaceutical compositions for the treatment of breast cancer comprising at least one polypeptides and a physiologically acceptable carrier are provided, wherein the polypeptide comprises an immunogenic portion of a breast tumor protein or a variant thereof, the breast tumor protein being encoded by a DNA molecule having a partial sequence selected from the group consisting of: (a) nucleotide sequences recited in SEQ ID NOS: 1, 2, 4–9, 11–16, 18–23, 25–44, 53 and 54, (b) complements of said nucleotide sequences, and (c) sequences that hybridize to a sequence of (a) or (b) under moderately stringent conditions. The invention also provides vaccines for the treatment of breast cancer comprising such polypeptides in combination with a non-specific immune response; enhancer, together with pharmaceutical compositions and vaccines comprising at least one DNA molecule having a partial sequence provided in SEQ ID NOS: 1, 2, 4–9, 11–16, 18–23, 25–44, 53 and 54.

In yet another aspect, methods are provided for inhibiting the development of breast cancer in a patient, comprising administering an effective amount of at least one of the above pharmaceutical compositions and/or vaccines.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the immunotherapy of breast cancer. The inventive compositions are generally isolated polypeptides that comprise at least a portion of a breast tumor protein. Also included within the present invention are molecules (such as an antibody or fragment thereof) that bind to the inventive polypeptides. Such molecules are referred to herein as "binding agents."

In particular, the subject invention discloses polypeptides comprising at least a portion of a human breast tumor protein, or a variant thereof, wherein the breast tumor protein includes an amino acid sequence encoded by a DNA molecule including a sequence selected from the group consisting of: nucleotide sequences recited in SEQ ID NOS: 1–67, the complements of said nucleotide sequences, and variants thereof. As used herein, the term "polypeptide" encompasses amino acid chains of any length, including full length proteins, wherein the amino acid residues are linked by covalent peptide bonds. Thus, a polypeptide comprising a portion of one of the above breast proteins may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human breast tumor protein is a portion that is capable of eliciting an immune response in a patient inflicted with breast cancer and as such binds to antibodies present within sera from a breast cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of breast cancer patients. Methods for preparing and identifying immunogenic portions of antigens of known sequence are well known in the art and include those summarized in Paul, *Fundamental Immunology*, $3^{rd}$ ed., Raven Press, 1993, pp. 243–247.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. The identity of polypeptides may be determined using computer algorithms well known to those of skill in the art, such as Megalign, using default parameters.

For breast tumor polypeptides with immunoreactive properties, variants may, alternatively, be identified by modifying the amino acid sequence of one of the above polypeptides, and evaluating the immunoreactivity of the modified polypeptide. For breast tumor polypeptides useful for the generation of diagnostic binding agents, a variant may be identified by evaluating a modified polypeptide for the ability to generate antibodies that detect the presence or absence of breast cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gLn, asn, ser, thr; (2) cys, ser, tyr, thr; (3) val, ile, leu, met, ala, phe; (4) lys, arg, his; and (5) phe, tyr, trp, his.

Variants of the inventive polypeptides may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. The identity of nucleotide sequences may be determined by comparing sequences using computer algorithms well known to those of skill in the art, such as Megalign, using default parameters. Such variant nucleotide sequences will generally hybridize to the recite nucleotide sequence under moderately stringent conditions. As used herein, "moderately stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The breast tumor proteins of the present invention, and DNA molecules encoding such proteins, may be isolated from breast tumor tissue using any of a variety of methods well known in the art. DNA sequences corresponding to a gene (or a portion thereof) encoding one of the inventive breast tumor proteins may be isolated from a breast tumor cDNA library using a subtraction technique as described in detail below. Examples of such DNA sequences are provided in SEQ ID NOS: 1–67. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.*, 51:263, 1987; Erlich ed., *PCR Technology*, Stockton Press, N.Y, 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA*, 2:183, 1983).

The breast tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Caif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related. aspect, the present invention provides fusion proteins comprising a first and a second inventive polypeptide or, alternatively, a polypeptide of the present invention and a known breast tumor antigen, together with variants of such fusion proteins.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide. linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.*, 336:86–91 (1997)).

Polypeptides of the present invention that comprise an immunogenic portion of a breast tumor protein may generally be used for immunotherapy of breast cancer, wherein the polypeptide stimulates the patient's own immune response to breast tumor cells. In further aspects, the present invention provides methods for using one or more of the immunoreactive polypeptides encoded by a DNA molecule having a sequence provided in SEQ ID NOS: 1–67 (or fusion proteins comprising one or more such polypeptides and/or DNA encoding such polypeptides) for immunotherapy of breast cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or DNA molecules encoding such polypeptides) may be used to treat breast cancer or to inhibit the development of breast cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, wherein the non-specific immune response enhancer is capable of eliciting or enhancing an immune response to an exogenoius antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a breast tumor cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against breast tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of breast cancer. For example, cells of the immune system, such as T cells, may be isolated from the peripheral blood of a patient, using a commercially available cell separation system, such as CellPro Incorporated's (Bothell, WA) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides of the present invention may also, or alternatively, be used to generate binding agents, such as antibodies or fragments thereof, that are capable of detecting metastatic human breast tumors. Binding agents of the present invention may generally be prepared using methods known to those of ordinary skill in the art, including the representative procedures described herein. Binding agents are capable of differentiating between patients with and without breast cancer, using the representative assays described herein. In other words, antibodies or other binding agents raised against a breast tumor protein, or a suitable portion thereof, will generate a signal indicating the presence of primary or metastatic breast cancer in at least about 20% of patients afflicted with the disease, and will generate a negative signal indicating the absence of the disease in at least about 90% of individuals without primary or metastatic breast cancer. Suitable portions of such breast tumor proteins are portions that are able to generate a binding agent that indicates the presence of primary or metastatic breast cancer in substantially all (i.e., at least about 80%, and preferably at least about 90%) of the patients for which breast cancer would be indicated using the full length protein, and that indicate the absence of breast cancer in substantially all of those samples that would be negative when tested with full length protein. The representative assays described below, such as the two-antibody sandwich assay, may generally be employed for evaluating the ability of a binding agent to detect metastatic human breast tumors.

The ability of a polypeptide prepared as described herein to generate antibodies capable of detecting primary or metastatic human breast tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic breast cancer for the presence of a polypeptide that binds to the generated antibodies. Such test assays may be performed, for example, using a representative procedure described below. Polypeptides that generate antibodies capable of detecting at least 20% of primary or metastatic breast tumors by such procedures are considered to be useful in assays for detecting primary or metastatic human breast tumors. Polypeptide specific antibodies may be used alone or in combination to improve sensitivity.

Polypeptides capable of detecting primary or metastatic human breast tumors may be used as markers for diagnosing breast cancer or for monitoring disease progression in patients. In one embodiment, breast cancer in a patient may be diagnosed by evaluating a biological sample obtained from the patient for the level of one or more of the above polypeptides, relative to a predetermined cut-off value. As used herein, suitable "biological samples" include blood, sera and urine.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without breast cancer. In general, a sample generating a signal that is three standard deviations above the predetermined cut-off value is considered positive for breast cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of breast cancer. In this embodiment, assays as described above for the diagnosis of breast cancer may be performed over time, and the change in the level of reactive polypeptide(s) evaluated. For example, the assays may be performed every 24–72 hours for a period of 6 months to 1 year, and thereafter performed as needed. In general, breast cancer is progressing in those patients in whom the level of polypeptide detected by the binding agent increases over time. In contrast, breast cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J Immunol;* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate breast tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible;

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify breast tumor-specific cDNA derived from a biological sample, wherein at least one of the oligonucleotide primers is specific for a DNA molecule encoding a breast tumor protein of the present invention. The presence of the amplified cDNA is then detected using techniques well known in the art, such as gel electrophoresis. Similarly, oligonucleotide probes specific for a DNA molecule encoding a breast tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 60%, preferably at least about 75% and more preferably at least about 90%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule having a partial sequence selected from SEQ ID NOS: 1–67. Preferably, oligonucleotide probes for use in the inventive diagnostic methods comprise at least about 15 contiguous oligonucleotides of a DNA molecule having a partial sequence provided in SEQ ID NOS: 1–67. Techniques for both PCR based assays and hybridization assays are well known in the art (see, for example, Mullis et al. Ibid; Ehrlich, Ibid). Primers or probes may thus be used to detect breast tumor-specific sequences in biological samples, including blood, urine and/or breast tumor tissue.

The following Examples are offered by way of illustration and not by way of limitation.

EXAMPLES

Example 1

Isolation and Characterization of Breast Tumor Polypeptides

This Example describes the isolation of breast tumor polypeptides from a breast tumor cDNA library.

A human breast tumor cDNA expression library was constructed from a pool of breast tumor poly $A^+$ RNA from three patients using a Superscript Plasmid System for cDNA Synthesis and Plasmid Cloning kit (BRL Life Technologies, Gaithersburg, Md. 20897) following the manufacturer's protocol. Specifically, breast tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BstX I adaptors (Invitrogen, San Diego, Calif.) and digested with NotI. Following size fractionation with Chroma Spin-1000 columns (Clontech, Palo Alto, Calif. 94303), the cDNA was ligated into the EcoRI/NotI site of pCDNA3.1 (Invitrogen) and transformed into ElectroMax $E.$ $coli$ DH10B cells (BRL Life Technologies) by electroporation.

Using the same procedure, a normal human breast cDNA expression library was prepared from a pool of four normal breast tissue specimens. The cDNA libraries were characterized by determining the number of independent colonies, the percentage of clones that carried insert, the average insert size and by sequence analysis. The breast tumor library contained $1.14 \times 10^7$ independent colonies, with more than 90% of clones having a visible insert and the average insert size being 936 base pairs. The normal breast cDNA library contained $6 \times 10^6$ independent colonies, with 83% of clones having inserts and the average insert size being 1015 base pairs. Sequencing analysis showed both libraries to contain good. complex cDNA clones that were synthesized from mRNA, with minimal rRNA and mitochondrial DNA contamination sequencing.

cDNA library subtraction was performed using the above breast tumor and normal breast cDNA libraries, as described by Hara et al. (*Blood,* 84:189–199, 1994) with some modifications. Specifically, a breast tumor-specific subtracted cDNA library was generated as follows. Normal breast cDNA library (70 µg) was digested with EcoRI, NotI, and SfuI, followed by a filling-in reaction with DNA polymerase Klenow fragment. After phenol-chloroform extraction and ethanol precipitation, the DNA was dissolved in 100 µl of $H_2O$, heat-denatured and mixed with 100 µl (100 µg) of Photoprobe biotin (Vector Laboratories, Burlingame, Calif.), the resulting mixture was irradiated with a 270 W sunlamp on ice for 20 minutes. Additional Photoprobe biotin (50 µl) was added and the biotinylation reaction was repeated. After extraction with butanol five times, the DNA was ethanol-precipitated and dissolved in 23 µl $H_2O$ to form the driver DNA.

To form the tracer DNA, 10 µg breast tumor cDNA library was digested with BamHI and XhoI, phenol chloroform extracted and passed through Chroma spin-400 columns (Clontech). Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenolchloroform extraction. This process was repeated three more times. Subtracted DNA was precipitated, dissolved in 12 µl $H_2O$, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax $E.$ $coli$ DH10B cells by electroporation to generate a breast tumor specific subtracted cDNA library.

To analyze the subtracted cDNA library, plasmid DNA was prepared from 100 independent clones, randomly picked from the subtracted breast tumor specific library and characterized by DNA sequencing with a Perkin Elmer/Applied Biosystems Division Automated Sequencer Model 373A (Foster City, Calif). Thirty-eight distinct cDNA clones were found in the subtracted breast tumor-specific cDNA library. The determined 3' cDNA sequences for 14 of these clones are provided in SEQ ID NO: 1–14, with the corresponding 5' cDNA sequences being provided in SEQ ID NO: 15–28, respectively. The determined one strand (5' or 3') cDNA sequences for the remaining clones are provided in SEQ ID NO: 29–52. Comparison of these cDNA sequences with known sequences in the gene bank using the EMBL and GenBank databases (Release 97) revealed no significant homologies to the sequences provided in SEQ ID NO: 3, 10, 17, 24 and 45–52. The sequences provided in SEQ ID NO: 1, 2, 4–9, 11–16, 18–23, 25–41 , 43 and 44 were found to show at least some degree of homology to known human genes. The sequence of SEQ ID NO: 42 was found to show some homology to a known yeast gene.

To determine mRNA expression levels of cDNA clones from subtracted library, cDNA clones from the breast subtraction described above were randomly picked and colony PCR amplified and their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Fifteen distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NO: 53–67. Comparison of the sequences of SEQ ID NO: 53 and 54 with those in the gene bank as described above, revealed some homology to previously identified human genes. No significant homologies were found to the sequences of SEQ ID NO: 55–67.

Example 2

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronmium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole-water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated DNA molecule consisting of SEQ ID NO: 55.
2. An isolated DNA molecule consisting of SEQ ID NO: 61.
3. An isolated DNA molecule consisting of SEQ ID NO: 62.
4. An isolated DNA molecule consisting of SEQ ID NO: 63.
5. An isolated DNA molecule consisting of SEQ ID NO: 64.
6. An isolated DNA molecule consisting of SEQ ID NO: 65.
7. An isolated DNA molecule consisting of SEQ ID NO: 67.
8. An vector comprising a DNA molecule according to any one of claims 1 and 2–7.
9. A host cell transformed with the vector of claim 8.
10. The host cell of claim 9 wherein the host cell is selected from the group consisting of *E. coli*, yeast and mammalian cell lines.

* * * * *

UNITED STATES PATENT AND TRADEMARK OFFICE
CERTIFICATE OF CORRECTION

PATENT NO.     : 6,379,951 B1
DATED          : April 30, 2002
INVENTOR(S)    : Steven G. Reed et al.

It is certified that error appears in the above-identified patent and that said Letters Patent is hereby corrected as shown below:

<u>Column 64,</u>
Line 14, "An vector comprising" should read -- A vector comprising --.

Signed and Sealed this

Fourth Day of February, 2003

JAMES E. ROGAN
*Director of the United States Patent and Trademark Office*